(12) United States Patent
Kaneko

(10) Patent No.: US 6,270,638 B1
(45) Date of Patent: Aug. 7, 2001

(54) PYRO-SENSOR AND PYRO-CONTROL CIRCUIT

(75) Inventor: Masaya Kaneko, Kumagaya (JP)

(73) Assignee: Kabushiki Kaisha Riken, Tokyo (JP)

( * ) Notice: Subject to any disclaimer, the term of this patent is extended or adjusted under 35 U.S.C. 154(b) by 0 days.

(21) Appl. No.: 09/081,959

(22) Filed: May 19, 1998

(30) Foreign Application Priority Data

May 23, 1997 (JP) .................................................. 9-150007
Jun. 30, 1997 (JP) .................................................. 9-189302

(51) Int. Cl.[7] .................................................. G01N 27/407
(52) U.S. Cl. .......................... 204/424; 204/406; 219/486; 219/501
(58) Field of Search .................................... 204/408, 426, 204/424, 425, 406; 219/209, 476, 478, 543, 486, 501

(56) References Cited

U.S. PATENT DOCUMENTS

| | | | |
|---|---|---|---|
| 4,875,990 | * 10/1989 | Kodachi et al. | 204/408 |
| 5,104,513 | * 4/1992 | Lee et al. | 204/425 |
| 5,184,500 | * 2/1993 | Kroma et al. | 73/23.2 |
| 5,434,551 | 7/1995 | Chen et al. | |
| 5,504,307 | * 4/1996 | Hayashi et al. | 219/543 |
| 5,717,136 | * 2/1998 | Aoi et al. | 73/204.26 |

FOREIGN PATENT DOCUMENTS

0878707 * 11/1998 (EP).

OTHER PUBLICATIONS

Patent Abstracts of Japan, vol. 5, No. 48 (P–55), Apr. 7, 1981 and JP 56 004045 A (Nissan Motor Co.), Jan. 16, 1981.
Patent Abstracts of Japan, vol. 9, No. 265 (P–399), Oct. 23, 1985 and JP 60 114758 A (Fujikura), Jun. 21, 1985.

* cited by examiner

Primary Examiner—Robert J. Warden, Sr.
Assistant Examiner—Kaj K. Olsen
(74) Attorney, Agent, or Firm—Hopgood, Calimafde, Judlowe & Mondolino LLP

(57) ABSTRACT

A main heater consisting of first and second fever areas and auxiliary heater arranged on an insulator substrate to maintain a precise sensing temperature. Grounded first fever area is contiguous with second fever area and grounded auxiliary heater, with the resistance ratio of first fever area and second fever area identical to that of the third resistor and the second resistor in bridge circuit control. Pyro-sensor or limit current type oxygen sensor capable of maintaining a high temperature, for example 400° C., operates within the high temperature maintained by the main heater, and DC—DC converter for isolating a first power supply, which supplies electric power to the heater from second power supply. Leakage current of the insulator substrate will not be generated as the insulator substrate deteriorates, thereby protecting the sensor cell leakage current from the heater.

10 Claims, 6 Drawing Sheets

FIG. 1 (AMENDED) (PRIOR ART)
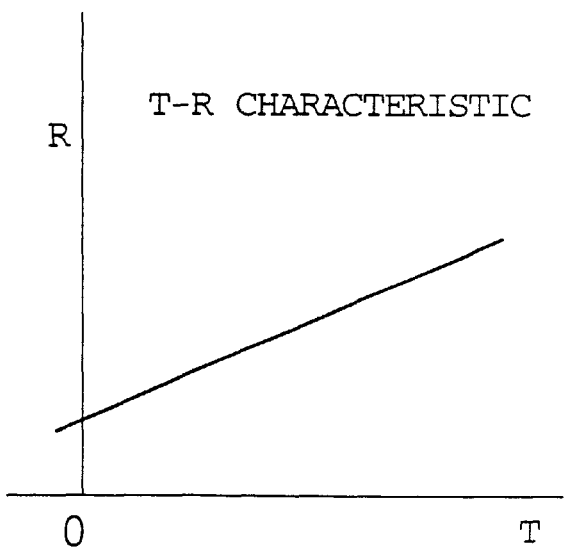
FIG. 2 (AMENDED) (PRIOR ART)
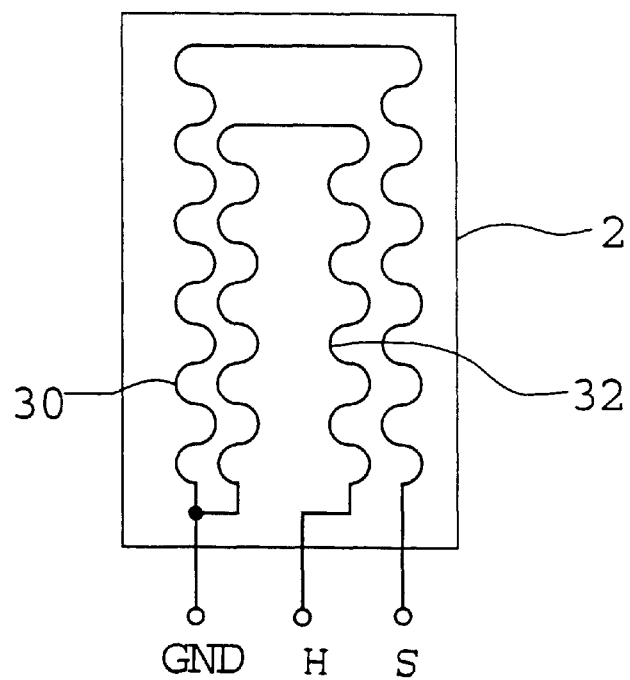

FIG. 3 (AMENDED)
(PRIOR ART)
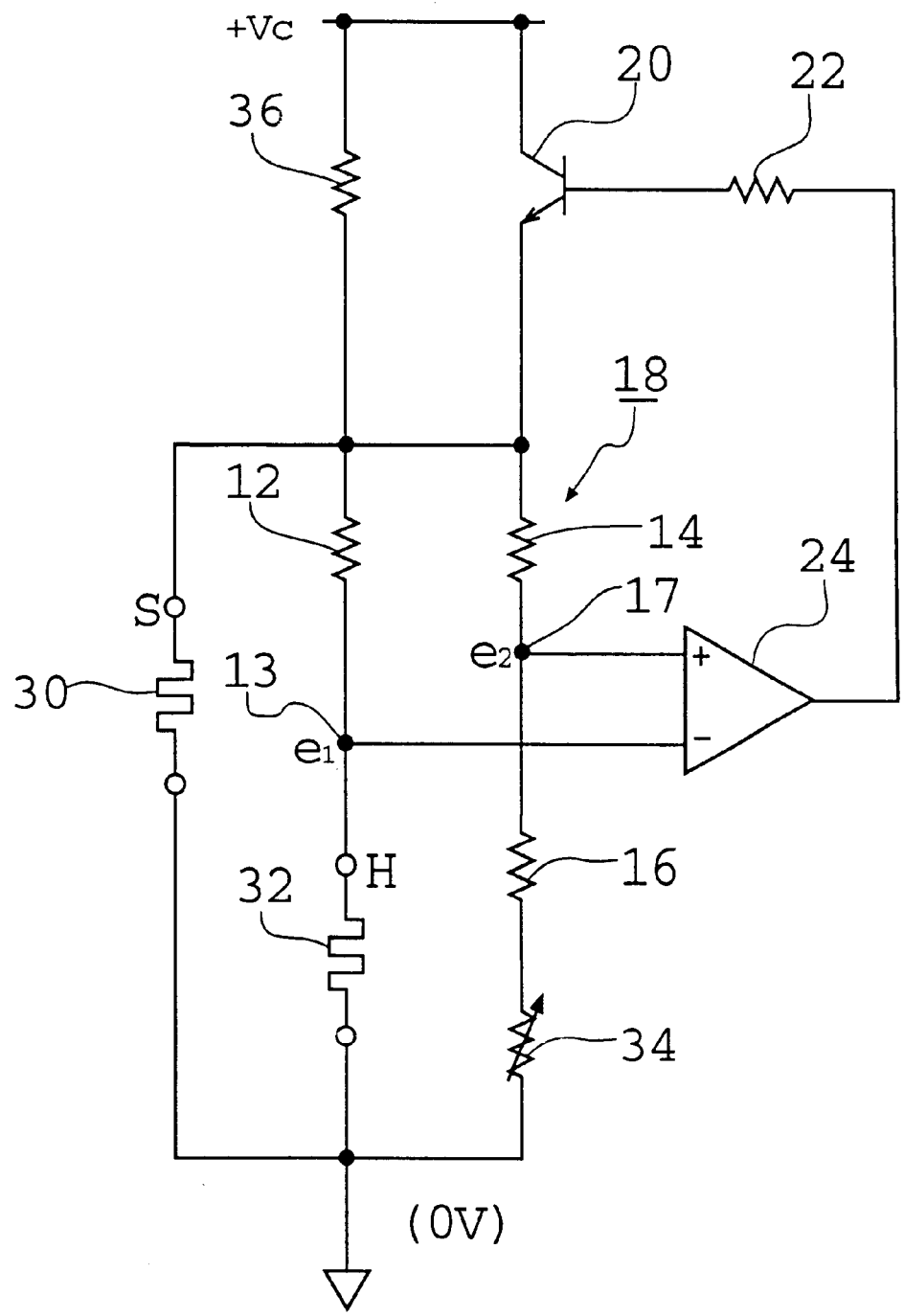

FIG. 4 (PRIOR ART) (AMENDED)
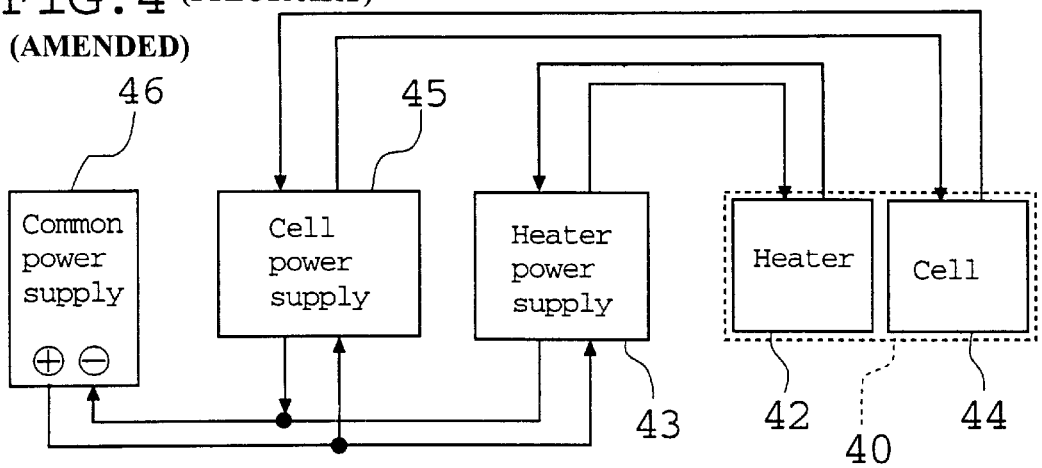
FIG. 5 (AMENDED) (PRIOR ART)
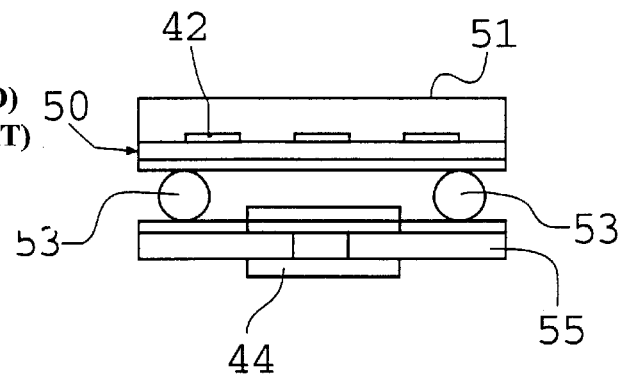
FIG. 6 (AMENDED) (PRIOR ART)

FIG. 8 (AMENDED)
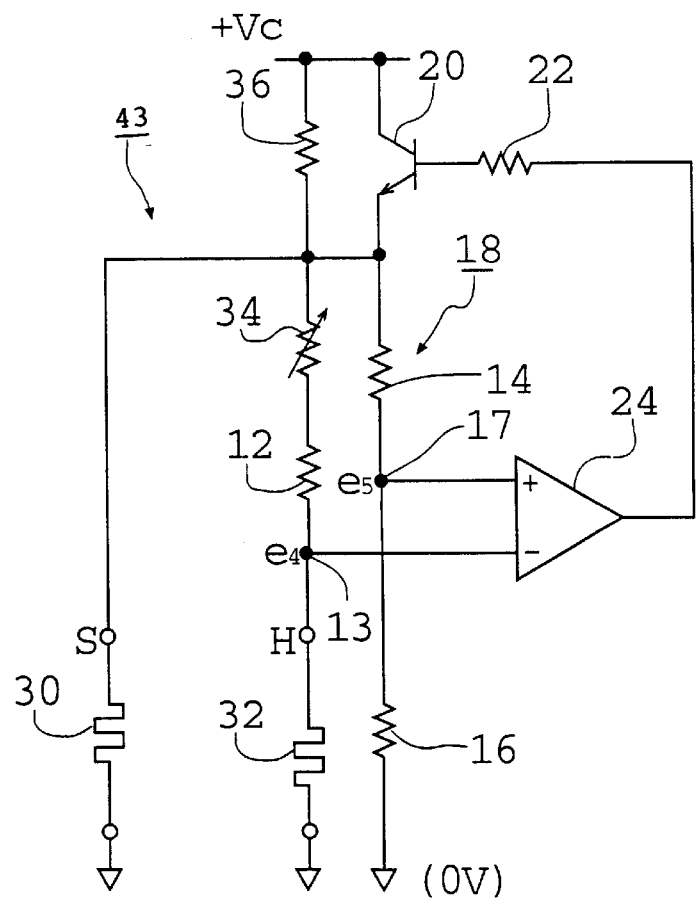

PYRO-SENSOR AND PYRO-CONTROL CIRCUIT

The present invention relates to a pyro-sensor such as oxygen and NOx sensors, a heater therefor and a pyro-control circuit.

BACKGROUND OF THE INVENTION

In a pyro-sensor such as oxygen and NOx sensors in which a sensing portion is heated by the heater, the characteristics of the pyro-sensor will be changed depending on a heater's itself temperature variation or a temperature variation of the heater due to the temperature variation around the environment. For example, a platinum thin film heater changes its resistance in response to temperature as shown in T (temperature)-R (resistor) characteristics of FIG. 1.

As a conventional heater temperature control method, for example, JP-A-60-114758 official gazette has been proposed to maintain temperature of the pyro-sensor to high temperature value. This method measures an environmental temperature by disposing a temperature sensor such as thermocouples or a thermistor adjacent to the sensor, and a load voltage to the heater is controlled as the result to maintain a sensor temperature to a predetermined value. In this case, the temperature sensor that ambient air temperature is only measured should be necessary, and a sensor's structure becomes much more complex, and it results in an expensive cost.

FIGS. 2 and 3 show another heater for the pyrosensor and its pyro-control circuit disclosed in Japanese Patent Application No. 8-298267 that is filed by the inventor on Oct. 22, 1996. In FIG. 2, a main heater 30 of platinum thin film is mounted on an insulator substrate 2 in alignment with a detective or sensing area, and an auxiliary heater 32 of platinum thin film is also arranged inside the main heater 30.

In FIG. 3, a collector of a transistor 20 is connected to the positive line voltage +Vc line, and its emitter is grounded through a bridge circuit 18 and the main heater 30. A first resistor 12 of the bridge circuit 18 is serially connected to the auxiliary heater 32 at a node 13, and its second resistor 14 is serially connected to its third resistor 16 and a variable resistor 34 through a node 17.

These nodes 13 and 17 are respectively connected to inputs of an operational amplifier 24. An output of the amplifier 24 is connected to the base of the transistor 20 through a protection resistor 22. The resistor 36 for supplying an early voltage to the bridge circuit 18 upon triggering is connected between the collector and emitter of the transistor 20.

In FIG. 3, the transistor 20 is so controlled by the amplifier 24 that the electric potential e1 of the node 13 is identical to that e2 of node 17 to maintain the temperature of the auxiliary heater 32 to a fixed or predetermined value.

For example, when the temperature of the auxiliary heater 32 is lower than the predetermined temperature value or e1<e2, the output voltage of the amplifier 24 is raised, and the main heater 30 and the auxiliary heater 32 are further heated to maintain the predetermined temperature condition.

In FIG. 2, the leakage current may flow to the auxiliary heater by the potential difference induced between the main and auxiliary heaters when the insulation of the insulator substrate arranged on the main and auxiliary heaters is deteriorated by, for example, aging. Therefore, though a configuration of the conventional pyro-control circuit is simple, the electric potential e1 will be increased by the leakage current, and the temperature of the auxiliary heater 32 has a problem to decrease less than the predetermined value.

FIG. 4 shows a block diagram of another conventional pyro-sensor. In FIG. 4, a common power supply 46 is provided to heat a heater 42 in a sensor 40 through first power supply 43, and to supply an applied voltage to a cell 44 in the sensor 40 through second power supply 45.

FIG. 5 is a cross-sectional top view to show an example of the sensor 40. In this drawing, a platinum thin film heater 42 is mounted or affixed on, for example, one surface of an insulator substrate 50, and its entire surface is covered with an insulating material 51 having the heat proof and corrosion tolerant characteristics. A cell substrate 55 for supporting the cell 44 is mounted on other side of the insulator substrate 50 through an insulation spacer 53.

When the above common power supply 46 drives the sensor 40 having, for example, a structure of FIG. 5, the deterioration or contact of the insulation characteristics between the heater 42 and the cell 44 may be generated by aging, and it is afraid that an unusual leakage current flows therebetween. This leakage current degrades the characteristics of the fresh sensor, and it is one of the causes which make reliability decline.

In other words, in the limit current type oxygen sensor having the structure like FIG. 5, the insulation characteristics between the heater 42 and the cell 44 is supposed to be degraded, because first power supply 43 and second power supply 45 are directly connected to the common power supply 46, a leakage current is generated regardless of more or less therebetween, one current loop (see FIG. 6) is generated through common ground both of power supplies. Then, the output of the sensor go wrong or the deterioration and reliability of the sensor is degraded.

Accordingly, it is an object of the invention to provide a high-reliable heater for the pyro-sensor and its pyro control circuit in which any leakage current doesn't occur even if the electric insulation of the insulator substrate deteriorates by aging, and then the main heater can maintain a predetermined temperature value as well as the auxiliary heater that serves as a temperature sensor.

It is another object of the invention to provide a method for driving a high-reliable sensor in which any leakage current from the heater is not generated, even if insulation characteristics between the heater and cell is degraded.

It is still another object of the invention to provide a driving method of the high reliable pyro-sensor that a current loop doesn't appear between the heater and the cell.

A main heater 30 consisting of first fever area 30a and second fever area 30b, and an auxiliary heater 32 are arranged on an insulator substrate to maintain a sensing portion, for example, 400° C. A grounded first fever area 30a is contiguously arranged between second fever area 30b and grounded auxiliary heater 32. An amplifier 24 controls a load voltage to a bridge circuit 18 containing the auxiliary heater 32, first, second and third resistors 12, 14, 16 and the main heater 30 based on the output of the bridge circuit 18. An inverting input of an amplifier 23 is connected to a node 13, and a non-inverting input thereof is connected to a node 17 of second and third resistors 14 and 16, and an output terminal is connected to the base or gate of the transistor 20 supplying the load voltage to the main heater 30. The resistance ratio of first fever area 30a and second fever area 30b is determined to be identical to that of third resistor 16 and second resistor 14. Pyro-sensor or limit current type oxygen sensor comprises a cell 44 capable of maintaining a high temperature, for example, 400° C. and a heater 42 for heating the cell 44 to the predetermined temperature. It firther comprises a DC-DC converter 48 isolating a first power supply 43 supplying electric power to the heater 42 from second power supply 45 applied a voltage to the cell 44.

A leakage current by deterioration of the insulator substrate is not generated, and temperature of a sensing portion is constantly maintained by the main heater to a high temperature. The sensor cell is protected from a leakage current from the heater from occurring.

A heater for the pyro-sensor according to the present invention is characterized in that a main heater consisting of first and second fever areas, and an auxiliary heater are arranged respectively on an insulator substrate; and first fever area is contiguously arranged between said second fever area and said auxiliary heater.

Therefore, for example, a common ground terminal connected to first fever area and the auxiliary heater is provided on one side or adjacent to the corner of a rectangular insulator substrate, and a power supply voltage is applied to a load terminal connected to second fever area so that the electric potential distribution or field between these heaters may be identical thereto.

According to the invention, there is provided a pyro-sensor comprising a cell and a heater for heating said cell in predetermined temperature, and characterized in that a first power supply supplying electric power to said heater is isolated from second power supply applying a voltage in said cell.

Said pyro-sensor is a limit current type oxygen sensor, and said first power supply is characterized by isolating from said second power supply through an insulation type DC-DC converter. Especially, the insulation type DC-DC converter is provided as first power supply to isolate first power supply from second power supply. The circuits relating to the heater and the cell are performed independent systems, respectively.

Because the current loop of second power supply 45 is insulated from that of first power supply 43 by the DC DC converter 48, specially, a transformer, any current never flows from the heater's loop to the cell's loop or vise versa, any leakage current doesn't appear and reliability of the sensor is improved even if insulation characteristics between the cell and the heater is degraded.

The foregoing and other objects, features and advantages of the invention will become apparent upon reading the following detailed description and drawings, in which:

FIG. 1 is the temperature (T) and resistor (R) characteristics of a platinum thin film heater;

FIG. 2 is a plan view of the conventional heater for the pyro-sensor; FIG. 3 shows a conventional bridge type pyro-control circuit;

FIG. 4 is the drive block diagram of the conventional pyro-sensor;

FIG. 5 shows the sensor structure used so far;

FIG. 6 shows the leakage current generated by the conventional driving method;

FIG. 8 is the circuit diagram which shows an embodiment of the pyro-control circuit according to the invention;

Figure 7:
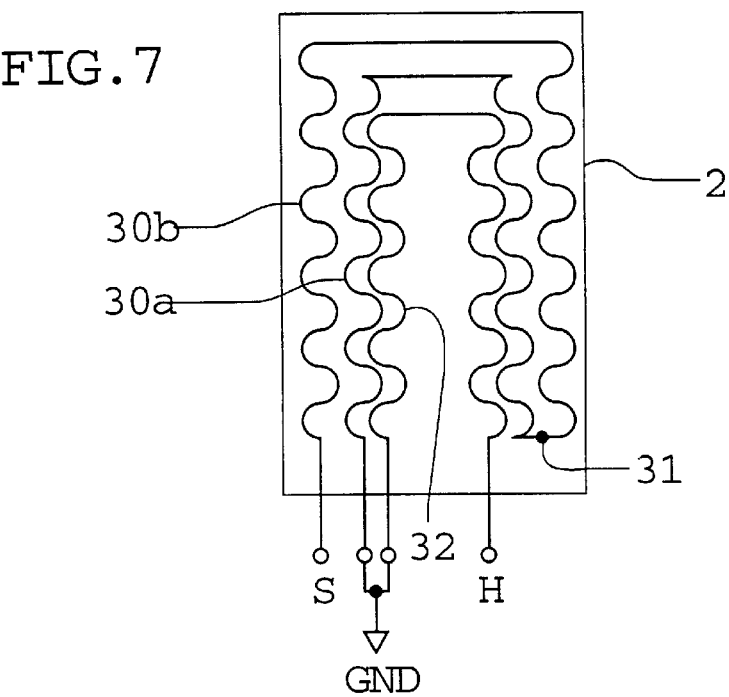
FIG. 7 is a plan view of the heater for the pyro-sensor according to the invention.

An embodiment of the present invention is described with reference to drawings as follows. FIG. 7 is a plan view that shows an embodiment of a heater for a pyro-sensor according to the invention. In FIG. 7, same numerals are denoted to those similar to components as shown in FIG. 1. A gas sensing portion (not shown) being heated to a high temperature is provided on a front surface of a zirconia substrate 2 having superior thermal conductivity, and two electrodes (not shown) are formed on both ends thereof.

A main heater 30 of platinum thin film in alignment with the sensing area is arranged on the back surface of the substrate 2. This main heater 30 contains a first fever area 30a and second fever area 30b with load terminal S and ground terminal GND being disposed on one or opposite side so that first and second fever areas are wired with at least in pair through a middle point 31. In this case, first fever area 30a and second fever area 30b are assumed to be identical resistance because the distribution of the cubic unit resistance therebetween is identical as well as same length. An auxiliary heater 32 of platinum thin film is arranged inside first fever area 30a.

Therefore, first fever area 30a is contiguously arranged on the zirconia substrate 2 between second fever area 30b and the auxiliary heater 32. Any leakage current is not influenced to the auxiliary heater 32 when the electric potential of each portion of the auxiliary heater 32 is identical to that of first fever area 30a adjoined thereto. Therefore, the resistance of first resistor 12 is predetermined to be generally identical to that of the auxiliary heater 32 at a predetermined temperature so that its resistor ratio is 1:1 to provide a maximum sensitivity.

FIG. 8 shows an embodiment of the pyro-control circuit of the heater for the pyro-sensor according to the invention. In FIG. 8, the same numerals are denoted to those in similar to members show in FIG. 3. A collector of an emitter follower connected transistor 20 is connected to the positive voltage +Vc power supply line. Its emitter is grounded through the main heater 30 consisting of first fever area 30a and second fever area 30b, and a bridge circuit 18 paralleled thereto. The first fever area 30a and second fever area 30b are wired on the insulator substrate 2 with the same quality of the material and the same length.

A current supplied from the transistor 20 is mostly supplied to the main heater 30 because an internal resistance of the bridge circuit 18 is higher than that of the main heater 30. In the bridge circuit 18, first resistor 12 and variable resistor 34 serially connected thereto are serially connected to the auxiliary heater 32 through a node 13, and second resistor 14 is connected to third resistor 16 through a node 17. The resistances of second resistor 14 and third resistor 16 are determined so that the ratio of their resistances may identical to that of second fever area 30b and first fever area 30a. The variable resistor 34 is also adjusted to the predetermined temperature.

These nodes 13 and 17 are connected to inverting and non inverting inputs of the operational amplifier 24, respectively. The output terminal of the amplifier 24 is connected to the base of the transistor 20 through a protection resistor 22. A pull-up resistor 36 for supplying an early voltage to the bridge circuit 18 upon triggering is connected between the collector and emitter of the transistor 20.

The basic action of the pyro-control circuit according to the invention is as follows. When the power supply to the control circuit is turned on, any differential output voltage doesn't occur in the bridge circuit 18, and a voltage, for example, 1 volt for the triggering is supplied to the bridge circuit 18 through the resistor 36. Very high resistance of the triggering resistor 36 is used to ignore the consumption of power supply because a current to the main heater 30 consisting of first fever area 30a and second fever area 30b is mainly supplied to the emitter follower 20.

Moreover, the resistances of the main heater 30 and the auxiliary heater 32 are relatively low under the room temperature or upon turning off the power supply, and then gradually increased to, for example, a target resistance corresponding to 400° C. upon turning on the power supply. Therefore, the amplifier 24 and the emitter follower 20 cause its power supply voltage to raise, and reach the balanced power supply voltage by the differential output voltage of the bridge circuit 18 generated by the increased resistance of the auxiliary heater 32. In other words, the transistor 20 is controlled by the amplifier 24 so that the electric potential e4 of the node 13 is identical to that e5 of the node 17 to maintain the temperature of the auxiliary heater 32 to the predetermined value.

Therefore, the output voltage of the amplifier 24 is raised with e4<e5 when temperature of the auxiliary heater 32 is lower than predetermined temperature. Then, the load voltage to the main heater 30 and the auxiliary heater 32 is raised through the transistor 20. The output voltage of the amplifier 24 is decreased by e4>e5 when temperature of the auxiliary heater 32 is higher than predetermined temperature.

Therefore, the load voltage to the main heater 30 and the auxiliary heater 32 is decreased to the predetermined value. Of course, almost all current is supplied to the main heater 30, and the main heater 30 is mainly heated.

The variable resistor 34 is the potentiometer or variable resistor which adjusts temperature of the auxiliary heater 32 to the requested value. Even if the insulation of zirconia substrate is temporarily deteriorated, the leakage current doesn't appear and doesn't influence to the auxiliary heater 32 because the electric potential distribution of first fever area 30a is identical to that of the auxiliary heater 32. In other words, heater temperature doesn't vary. The resistor 36 is a pull-up resistor by which electric potential e4 or e5 is not reduced to zero volts when the transistor 20 is turned off and then turned on.

In the circuit of FIG. 8, and targeted temperatures of the main and auxiliary heaters are so determined that the resistance ratio between a combined first resistor 12+variable resistor 34 and the auxiliary heater is identical to that between second resistor 14 and third resistor 16, and the resistance ratio between second resistor 14 and third resistor 16 is identical to that between second fever area 30b and first fever area 30a. Therefore, any leakage current caused by the insulation deterioration of the heater substrate doesn't occur.

Therefore, when the auxiliary heater 32 becomes, for example, 400° C., as the targeted load voltage is also supplied to the main heater 30 consisting of first fever area 30a and second fever area 30b, and the main heater 30 also becomes 400° C. at the same time. When a temperature variation of the main heater 30 is transferred to the auxiliary heater 32, the load voltage is varied to feed back the temperature variation to the auxiliary heater to return the targeted temperature. The targeted temperature may be controlled to, for example, 410° C. considering a heat loss of the substrate or film's thermal resistance resided with the gas sensing portion.

This insulator substrate is a ceramic substrate or silicon dioxide layer in which a thermal conductivity of aluminum nitride, silicone carbide, etc for use in the support plate of the sensing portion is close to that of metal. Alternatively, it may be a vaporized or coated film covered on a linear or meandering heater having generally rectangle or ellipse cross section printed or wired on a thermal insulation support body. Of course MOSFET may be used as the transistor except for bipolar type.

Figure 9:
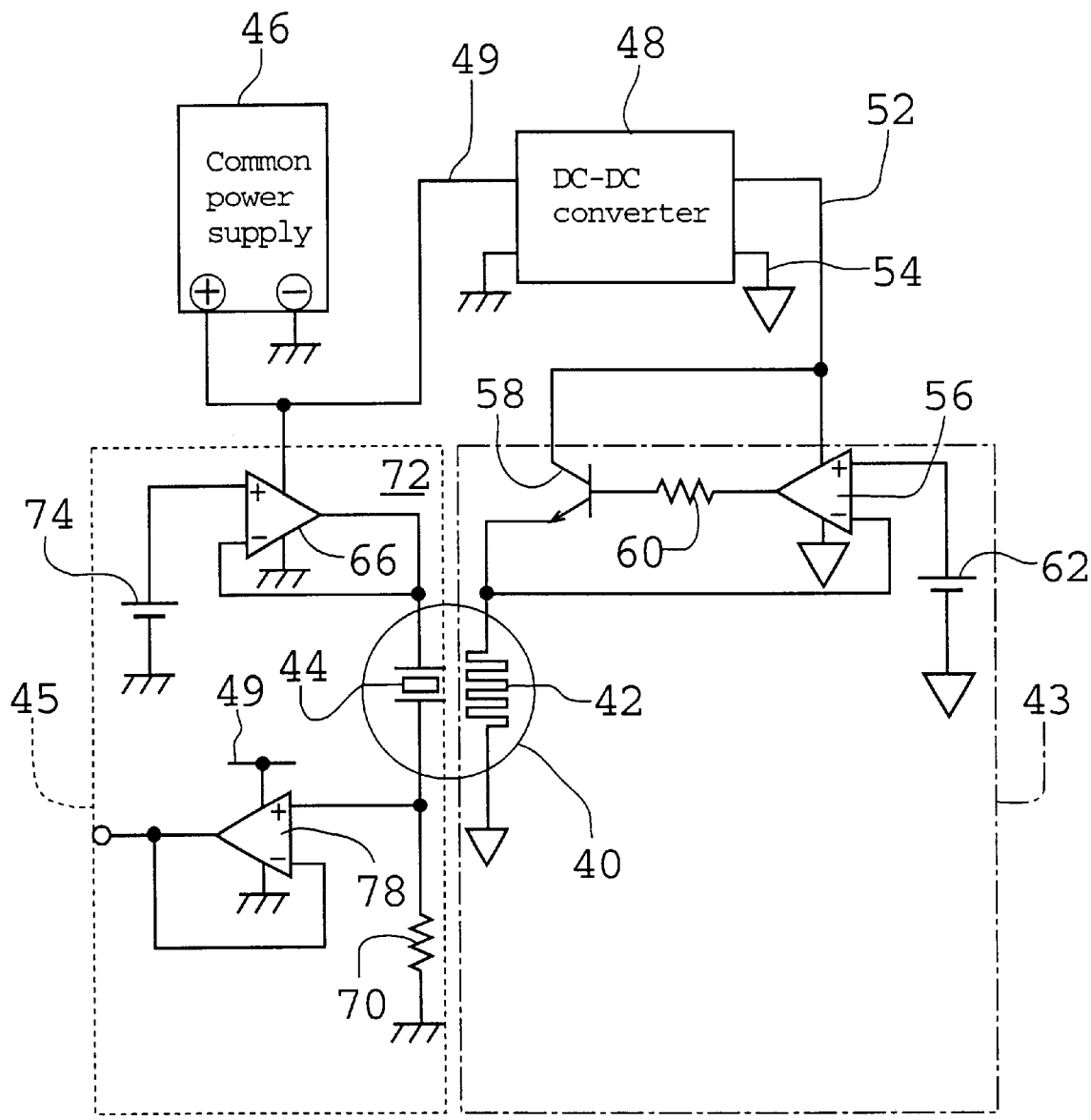
FIG. 9 shows a sensor drive block diagram according to the invention.

Another embodiment of the present invention is described in detail with reference to drawings as follows. FIG. 9 is the block diagram of the drive circuit of the pyro-sensor according to the invention. In this drawing, the point different from the conventional drive circuit is that a first power supply 43 to heat the heater 42 in the sensor 40 is isolated from the common power supply 46 by the DC-DC converter 48. This common power supply 46 supplies another applied voltage to the cell 44 in the sensor 40 as well through second power supply 45. Therefore, the cell 44 is maintained in the high temperature, for example, 400° C., and is set up in the detection condition of the gas.

For example, in the limit current type oxygen sensor, for example, a DC—DC converter 48 is provided between the common power supply 46 and first power supply 43 for controlling and heating the heater 42. That is, the power energy from the common power supply 46 is provided through a line 49 and returned ground line to a primary circuit (not shown) of the DC—DC converter 48. The primary circuit is isolated from a secondary circuit of the DC—DC converter 48 by a transformer. Then, a closed circuit of the current passing through the secondary circuit and the heater 42 is completely isolated, and a direct current from the common power supply 46 via the line 49 is also used for a detection power supply that applies a constant voltage to the cell. Thus, any leakage current is not generated by independently composing the heater and second power supply, respectively, even if insulation characteristics between the heater and the cell is degraded.

Figure 10:
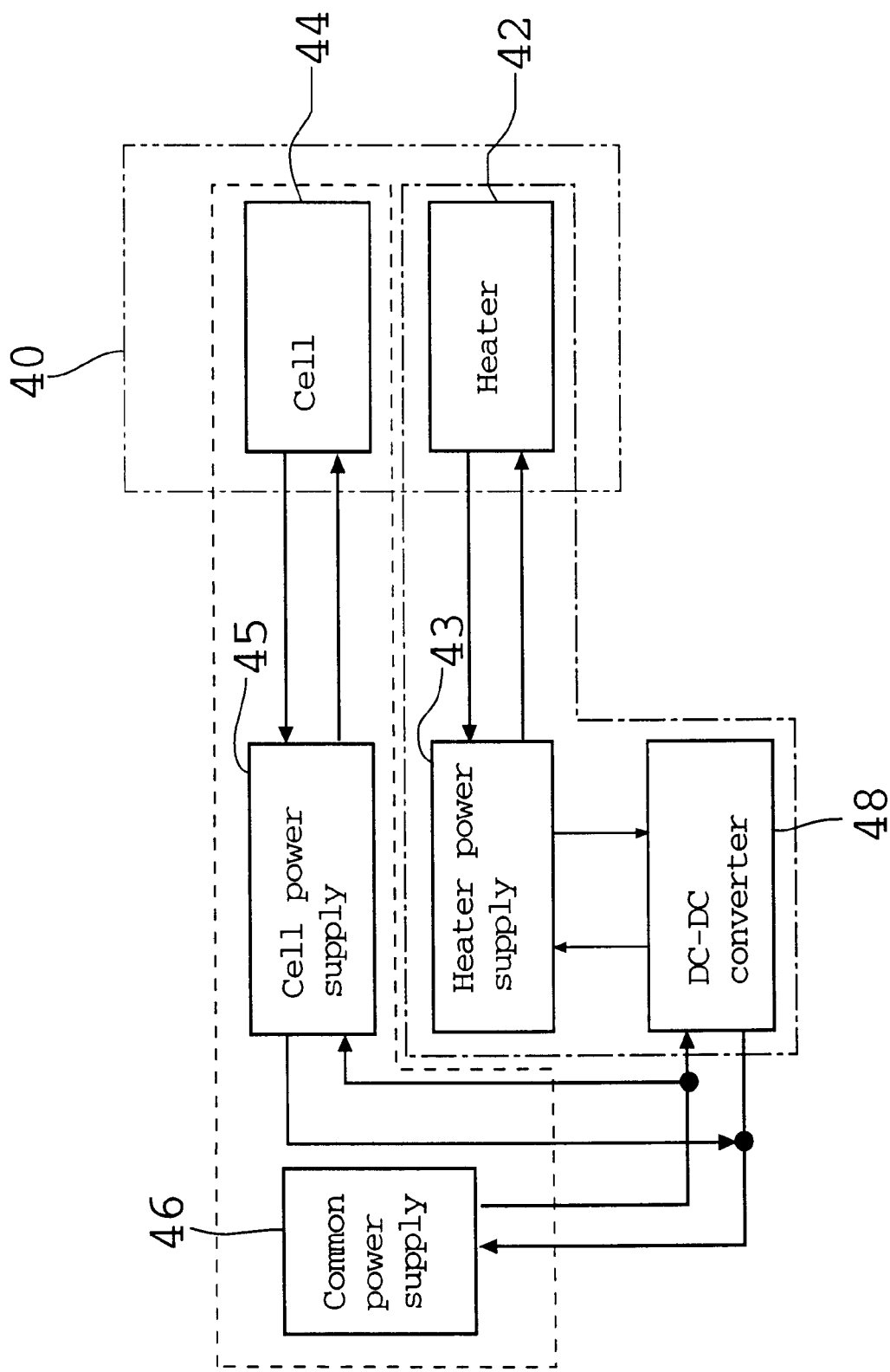
FIG. 10 is the circuit diagram which shows an embodiment of the drive circuit of the pyro-sensor according to the invention.

FIG. 10 is the circuit diagram showing an embodiment of the drive circuit of the pyro-sensor according to the invention. In FIG. 10, the same numerals are denoted to those similar to members shown in FIG. 5.

First, the DC—DC converter 48 comprises an insulation transformer (not shown) having a primary coil connected to the positive voltage line of the common power supply 46. Another terminal of the primary coil is connected to a power transistor (not shown) that switches the electric power supplied to the primary coil. On the other hand, the alternating voltage inducted by a secondary coil of the insulation transformer is rectified, and smoothed to provide an output voltage. The output voltage is partially negatively feedback to gate or base of the power transistor through a photocoupler (not shown).

Therefore, the switching frequency of the output voltage is controlled to maintain to the predetermined value after the V/F conversion, and supplied to first power supply 43 through the positive voltage line 52 and the ground line 54. The operational amplifier 56 controlling the voltage supplied to the heater 42 to the reference value is connected between the positive voltage line 52 and the ground line 54, and the transistor 58 of the emitter follower connection and the heater 42 are further connected in series therebetween.

In other words, the transistor 58 has a collector connected to the line 52, and an emitter connected to the heater 42 which is grounded. On the other hand, connected to the base of the transistor 58 is an output terminal of the operational amplifier 56 though a protection resistor 60. Moreover, the operational amplifier 56 has a non-inverting input connected to a reference voltage source 62, and an inverting input connected to the emitter of the transistor 58 and the heater 42.

This first power supply 43 can be configured to contain the DC-DC converter 48 in another embodiment. In this case, the heater 42 is connected between the lines 52 and 54. The voltage supplied to the heater 42 is constantly controlled after V/F conversion, through a negative feedback with the photo-coupler and so on.

Next, second power supply 45 comprises a voltage regulator circuit 72 directly connected to the common power supply 46, and supplying a constant voltage to the cell 44 and a detection resistor 70. This voltage regulator circuit 72 contains an operational amplifier 7, having an inverting input connected to a reference voltage source 74, and an output connected to its non-inverting input and the cell 44. Alternatively, the voltage regulator circuit 72 may be substituted with 3 terminal-type voltage regulator integrated circuit.

A node between the cell 44 and the detection resistor 70 are connected to the non-inverting input of another operational amplifier 78 by which its detection output is converted to a low impedance.

As described the above, the heater for the pyro-sensor and pyro-control circuit according to the invention doesnot generate any leakage current, and the temperature of the heater is not varied as the conventional heater even if the electric insulation of the heater substrate such as zirconia is deteriorated.

The value of second and third resistors can be set high compared with those of the conventional bridge type pyro control circuit. Because the ratio of second and third resistors can be set about 1:1, the change in the differential output voltage due to the temperature variation of the main heater consisting of first fever area 30a and second fever area 30b is efficiently obtained to provide a high precision temperature control. Moreover, temperature increase in the pyro-control circuit is limited, and the convergent time to the predetermined temperature is shortened than the conventional circuit. Of course, this ratio can be changed correspondinly to the resistance ratio of fever areas.

Moreover, the thermal conductivity of the substrate or film between the sensing portion and the heater is close to that of the metal and unified. Therefore, a temperature variation of the gas sensing portion or the heater due to the change in the ambient air temperature is compensated for, and the sensitivity characteristics of the gas sensing portion become stable. The auxiliary heater is mainly served as the temperature sensor. The main heater heats the sensing portion so that the bridge circuit is balanced. The leakage current doesn't occur from first fever area to the auxiliary heater, and rapid accurate temperature control becomes possible because first fever area electric potential distribution is identical to that of the auxiliary heater.

As described the above, the pyro-control circuit of the pyro-sensor of the invention uses two isolated power supplies, that is, direct current power supply and for example the DC—DC converter for the driving power supply. By making the independent power supply loops, respectively, any leakage current from the cell loop and another leakage current from the heater loop can be prevented completely.

What is claimed is:

1. A pyro-sensor comprising:
a cell;
a main healer comprising first and second fever areas for beating said cell to a predetermined temperature; and
an auxiliary heater, which is surrounded by said main heater;
said cell, said main heater and said auxiliary heater being arranged on an insulator substrate,
said first fever area contiguously arranged between said second fever area and said auxiliary heater, and
a first power supply supplying electric power to said main and auxiliary beaters and isolated from a second power supply that applies a voltage to said cell.

2. The pyro-sensor of claim 1, further comprising a control circuit for said heater comprising: a bridge circuit containing said auxiliary heater electrically parallel to said main heater and serially connected to a first resistor to provide a differential output node; and an amplifier connected to said differential output node for controlling a load voltage applied both to said bridge circuit and to said main heater based on said differential output of said bridge circuit.

3. The pyro-sensor of claim 2, wherein:
said bridge circuit comprises said first resistor, a second resistor, a third resistor, and said auxiliary heater; and
said amplifier has an inverting input connected to a first node between said first resistor and said auxiliary heater, a non-inverting input connected to a second node between said second and third resistors, and an output terminal connected to said main heater and said bridge circuit.

4. The pyro-sensor of claim 3, wherein said second and third resistors are set up so that the ratio of their resistance values is identical to that of said second and first fever areas.

5. The pyro-sensor of claim 4, wherein said bridge circuit is initially power supplied through a triggering resistor.

6. The pyro-sensor according to claim 1 wherein said pyro-sensor is a limit current type oxygen sensor.

7. The pyro-sensor according to claim 1 wherein said first power supply is isolated from said second power supply by an insulating type DC—DC converter.

8. A pyro-sensor comprising:
a cell;
a main heater comprising first and second fever areas for heating said cell to a predetermined temperature;
an auxiliary heater comprising at least one fever area;
a first power supply supplying electric power to said main and auxiliary heaters; and
a second power supply for applying a voltage to said cell;
said auxiliary heater having a lead for connecting to said first power supply;
said cell, said main heater, and said auxiliary heater being arranged on an insulator substrate,
said first fever area contiguously arranged between said second fever area and said auxiliary heater, and
said first power supply isolated from second power supply.

9. The pyro-sensor of claim 8, further comprising a control circuit for said main heater comprising;
a bridge circuit containing said auxiliary heater electrically parallel to said main heater and serially connected to a first resistor to provide a differential output node; and
an amplifier connected to said differential output node for controlling a load voltage applied both to said bridge circuit and to said main heater based on said differential output of said bridge circuit.

10. The pyro-sensor of claim 9, wherein:
said bridge circuit comprises said first resistor, a second resistor, a third resistor, and said auxiliamy heater; and
said amplifier has an inverting input connected to a first node between said first resistor and said auxiliay heater, a non-inverting input connected to a second node between said second and third resistors, and an output terminal connected to said main heater and said bridge circuit.

* * * * *